(12) United States Patent
Azorin

(10) Patent No.: US 7,825,156 B2
(45) Date of Patent: Nov. 2, 2010

(54) METHOD OF TREATING BIPOLAR DEPRESSION WITH A BENZAMIDE DERIVATIVE

(75) Inventor: Jean-Michel Azorin, Marseille (FR)

(73) Assignee: Copharms, Luxembourg (LU)

(*) Notice: Subject to any disclaimer, the term of this patent is extended or adjusted under 35 U.S.C. 154(b) by 0 days.

(21) Appl. No.: 12/013,128

(22) Filed: Jan. 11, 2008

(65) Prior Publication Data

US 2008/0188537 A1 Aug. 7, 2008

Related U.S. Application Data

(60) Provisional application No. 60/899,045, filed on Feb. 2, 2007.

(51) Int. Cl.
*A61K 31/40* (2006.01)
*A61K 31/55* (2006.01)
*A61K 31/445* (2006.01)
*A61K 31/19* (2006.01)
*A61K 31/135* (2006.01)
*A61K 33/00* (2006.01)

(52) U.S. Cl. .................. 514/428; 514/217; 514/321; 514/557; 514/649; 424/610

(58) Field of Classification Search .................. 514/428, 514/217, 321, 557, 649; 424/610
See application file for complete search history.

(56) References Cited

U.S. PATENT DOCUMENTS 4,401,822 A 8/1983 Thominet et al.
6,187,807 B1* 2/2001 Perrault et al. .............. 514/428
2003/0130334 A1* 7/2003 Muller ....................... 514/406

OTHER PUBLICATIONS

Aetna InteliHealth (intelihealth.com [online], www.intelihealth.com, Jul. 2006 [retrieved on Dec. 12, 2008]. Retrieved from the Internet: <URL: http://www.intelihealth.com/IH/ihtIH/WSIHW000/9339/9803.html.).*
Science Daily ([online], www.sciencedaily.com, Jul. 2005 [retrieved Dec. 12, 2008]. Retrieved from the Internet: <URL: http://www.sciencedaily.com/releases/2005/07/050704114242.htm).*
Manzaneque et al. (Aggressive Behavior, vol. 25, pp. 225-232; 1999).*
Galinsky et al. ["Basic Pharmacokinetics and Pharmacodynamics." in: Remington: The Science and Practice of Pharmacy (Baltimore, Lippincott Williams & Wilkins, 2006), p. 1171].*
Patani et al. (Chem Rev, vol. 96, No. 8, pp. 3147-3176; 1996).*
"Improvement of Schizophrenic Patients with Primary Negative Symptoms Treated with Amisulpride" Jean-Marie Danion, M.D. et al. Am J Psychiatry 156:4, Apr. 1999: 610-616.
"An Open Label Follow-Up Study on Amisulpride in the add-On Treatment of Bioplar I Patients" Mauro Giovanni Carta et al. Clinical practice and Epidemiology in Mental Health 2006, 2:19.
Neurochemical Characteristics of Amisulpride, an Atypical Dopamine D2D3 Receptor Antagonist with Both Presynaptic and Limbic Selectivity. H. Schoemaker et al. The Journal of Pharmacology and Experimental Therapeutics 1997, 280/1:83-97.
"Amisulpride Versus Placebo in the Medium-Term Treatment of the Negative Symptoms of Schizophrenia" H.Loo et al. Br J Psychiatry 1999, 170:18-22.

* cited by examiner

*Primary Examiner*—Raymond J Henley, III
(74) *Attorney, Agent, or Firm*—Dickstein Shapiro LLP

(57) ABSTRACT

A benzamide derivative, especially amisulpride, is used to prevent or treat bipolar depression of a patient suffering from bipolar disorder I or bipolar disorder II.

15 Claims, No Drawings

METHOD OF TREATING BIPOLAR DEPRESSION WITH A BENZAMIDE DERIVATIVE

This disclosure claims the priority of U.S. Provisional Patent Application US60/899,045 filed on Feb. 2, 2007

FIELD OF THE INVENTION

This invention is directed to a method for use of a benzamide derivative in preventing or treating bipolar depression of a patient suffering from bipolar disorder I or bipolar disorder II. More particularly, this invention is directed to a method for use of amisulpride for preventing or treating bipolar depression. The invention also relates to a means for use in the method.

BACKGROUND OF INVENTION

The bipolar disorders are mood disorders in which a disturbance in mood is the predominant feature. Bipolar I disorder is characterized by one or more manic or mixed episodes, usually accompanied by major depressive episodes. Bipolar II disorder is distinguished by primarily major depressive episodes accompanied by at least spontaneous hypomanic episodes according to Diagnostics and Statistical Manual of Mental Disorders, Edition—IV, American Psychiatric Association, Washington D.C. (DSM-IV). Bipolar depression refers to the major depressive episodes that occur along the course of bipolar I and II disorder.

In the U.S., the prevalence of bipolar disorder is estimated to be 1 to 3.5%, evenly divided between men and women. The length of time between onset and symptoms with proper diagnosis and treatment is approximately 10 years. It is estimated that only 60% of those suffering from a bipolar disorder are receiving appropriate pharmacotherapy.

Although there is extensive and emerging literature guiding the treatment of the manic phase of bipolar I disorder as well as many approved compounds for the treatment of unipolar depression, the treatment of bipolar depression has not been widely studied and treatment guidelines are in their infancy. The use of currently available antidepressants for monotherapy for bipolar depression is often problematic as they may increase the "switch" into hypomania or mania from depression, or increase cycle acceleration. Further, patients can experience treatment-emergent mania with antidepressant monotherapy. The long term use of mood stabilizing medications such as lithium carbonate ($Li_2CO_3$) is common and may decrease the likelihood of these complications.

Amisulpride is a recent atypical antipsychotic with a pharmacological and clinical profile that differs from that of other atypical agents. Amisulpride (Solian®, Lorex, Sanofi-aventis), a benzamide derivative, is closely related to sulpiride, licensed for the treatment of schizophrenia and negative symptoms associated with schizophrenia. Amisulpride is a selective dopamine $D_2/D_3$ antagonist (*J Pharmacol Exp Ther* 1997, 280/1:83-97) and has been the most thoroughly evaluated atypical antipsychotic for the treatment of negative symptoms (*Br J Psychiatry* 1999, 170: 18-22; *Am J Psychiatry* 1999, 156/4: 610-616). Amisulpride recommended daily doses are 400-800 mg (maximum 1200 mg) for acute psychotic episodes, and 50-300 mg for patients with predominantly negative symptoms.

The synthesis of amisulpride is described in U.S. Pat. No. 4,401,822.

A literature search demonstrates that, as in the case with many other antipsychotic drugs, there has been a wide use of amisulpride as an add-on in many psychiatric disorders. In a few papers amisulpride has been used among other drugs as add-on to treatment for bipolar disorders.

Recently, the relapse rate in an open label follow-up study on amisulpride in the add-on treatment of bipolar I patients has been measured. Clinical Practice and Epidemiology in Mental Health 2006, 2:19. A statistically significant decrease in overall relapse rate was observed during the period of amisulpride therapy, but only manic episodes reached statistical significance.

SUMMARY OF THE INVENTION

Benzamide derivatives such as amisulpride, sulpiride and sultopride, or pharmaceutically acceptable salts, and mixtures thereof, are effective treatments of bipolar depression including depression symptoms associated with bipolar disorder I or bipolar disorder II in a patient.

DETAILED DESCRIPTION OF THE INVENTION

It has been unexpectedly been found that benzamide derivatives such as amisulpride, sulpiride or sultopride, or pharmaceutically acceptable salts and mixtures thereof are effective treatments for depressive patients suffering from bipolar disorders not responding or partially responding to drugs widely used for this condition, including but not limited to lithium, divalproate, clomipramine, fluoxetine and paroxetine.

More particularly, it has now been discovered that amisulpride or a pharmaceutically acceptable salt thereof is an effective treatment for depressive patients suffering from bipolar disorders not responding or partially responding to drugs widely used for this condition, including but not limited to lithium, divalproate, clomipramine, fluoxetine, and paroxetine.

According to the present invention is disclosed a method of treating bipolar depression in patients suffering from bipolar I or bipolar II disorders, comprising administering to a patient a therapeutically effective amount of benzamide derivatives of the general formula (I).

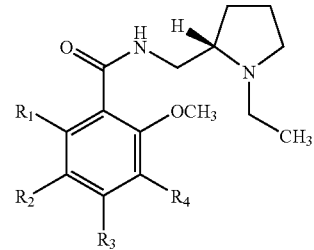

Formula (I)

(Ia) $R_1$ = H, $R_2$ = $SO_2C_2H_5$, $R_3$ = $NH_2$, $R_4$ = H.
(Ib) $R_1$ = H, $R_2$ = $SO_2NH_2$, $R_3$ = H, $R_4$ = H.
(Ic) $R_1$ = H, $R_2$ = $SO_2C_2H_5$, $R_3$ = H, $R_4$ = H.

Specific benzamide derivatives include, but are not limited to amisulpride (Ia), or 4-amino-N-[(1-ethylpyrrolidin-2-yl)methyl]-5-(ethylsulfonyl)-2-methoxybenzamide; sulpiride (Ib) or N-[(1-ethylpyrrolidin-2-yl)methyl]-2-methoxy-5-sulfamoyl-benzamide; sultopride (Ic) or N-[(1-ethylpyrrolidin-2-yl)methyl]-5-(ethylsulfonyl)-2-methoxybenzamide;

The present invention provides a method of treating bipolar depression by orally administering to a patient benzamide derivatives, preferably selected from the group consisting of amisulpride, sulpiride and sultopride or pharmaceutically acceptable salts thereof.

Other embodiments of the method include the use of a compound of benzamide derivatives and more particularly amisulpride or a pharmaceutically acceptable salt thereof, for the preparation of a medicament for treating bipolar depression in a patient suffering from bipolar disorders.

Another embodiment of the method include the use of a compound of benzamide derivatives and more particularly amisulpride or a pharmaceutically acceptable salt thereof, for the preparation of a medicament for treating bipolar depression in a patient suffering from bipolar disorder I.

Another embodiment of the method include the use of a compound of benzamide derivatives and more particularly amisulpride or a pharmaceutically acceptable salt thereof, for the preparation of a medicament for treating bipolar depression in a patient suffering from bipolar disorder II.

Another embodiment of the invention provides a method of treating bipolar depression in patients, suffering from bipolar disorder I or bipolar disorder II by oral administration of amisulpride.

Bipolar depressive patient is here defined as a patient with either Bipolar I Disorder, Most Recent Episode Depressed; Bipolar I Disorder, Most Recent Episode Mixed or Bipolar II Disorder (Recurrent Major Depressive Episodes With Hypomanic Episodes) (Classification 296.5×, 296.6×, and 296.89 respectively of DSM-IV).

Administration for gastrointestinal absorption can be by the oral or rectal route, such as by tablets and suppositories, respectively. It is also within the scope of the invention to provide liquid formulations, in particular aqueous formulations, for oral administration. A further route of administration is by intravenous or intramuscular injection in a liquid carrier such as physiological saline. Pharmaceutical compositions of the compounds of the invention suitable in the treatment of bipolar depression are described in literature and are marketed, albeit for different indications, in various countries.

The term "therapeutically effective amount" as defined in this invention means an amount of the compound which is effective in treating a patient for the named disorder or condition.

In one embodiment, bipolar depression may be treated by administering amisulpride to a patient in a dosage ranging from about 20 mg/day to about 800 mg/day.

In another embodiment, bipolar depression may be treated by administering amisulpride to a patient in a dosage ranging from about 50 mg/day to about 300 mg/day.

When given in such a dose, amisulpride exerts a clinically beneficial effect on bipolar depression. No deterioration of any other aspect of bipolar disorder, such as treatment-emergent mania was observed.

The following examples are intended for illustrative purposes only and are not meant to limit the invention in any manner:

EXAMPLES

Case 1

Female subject (42y) diagnosed with bipolar II disorder, recurrent major depressive episodes with hypomanic episodes). She is admitted for bipolar depression and amisulpride treatment of 200 mg/d is initiated. After 4 weeks of treatment with amisulpride, the depressive state started to markedly decrease and after 6 weeks it had disappeared completely. After 3 years of treatment with amisulpride 100 mg/d no manic or depressive recurrence had occurred.

Case 2

Female subject (36y) diagnosed with bipolar II disorder, recurrent major depressive episodes with hypomanic episodes). She is admitted for bipolar depression and amisulpride treatment of 100 mg/d is initiated. After 3 weeks of treatment with amisulpride the patient's depressive condition improved. After 4 years of treatment with amisulpride 100 mg/d any relapse has still not occurred.

Case 3

Male subject (32y), diagnosed with bipolar disorder I, most recent episode depressed. Upon admission at the hospital a treatment with amisulpride 100 mg/g was initiated. After 3 weeks of treatment, a significant improvement of the depressive disorder was observed. After 4 years of treatment with amisulpride 50 mg/d still no relapse has occurred.

Case 4

Male subject (27y) diagnosed with bipolar I disorder, most recent episode mixed. The patient is hospitalised for bipolar depression and treatment with amisulpride 150 mg/g initiated. The depressive disorder rapidly improved and had disappeared after 4 weeks. After 4 years of treatment with amisulpride 150 mg/d still no relapse has occurred.

Case 5

Female subject (54y), diagnosed with bipolar I disorder, most recent episode depressed, for the first time at the age of 47. The patient has been on lithium for about 3 years. She is compliant with her treatment and lithium serum levels remains stable around 0.7-0.9 mEq/L. She is admitted for bipolar depression with lithium serum level were 0.8 mEq/L. The day after she received an amisulpride treatment of 100 mg/d. After 3 weeks of treatment with amisulpride, the depressive state had started to vanish progressively and had disappeared completely after 6 weeks. After 3 years of treatment no manic or depressive recurrence had occurred.

Case 6

Male subject (35y), diagnosed with bipolar disorder I, most recent episode depressed, is hospitalized for manic state. His illness started 4 years ago. The patient suffers bipolar disorder type I. The patient has already shown two manic episodes. At entrance, he received divalproate at a dose of 1250 mg/d. After one month of treatment, the manic symptoms have disappeared, but suicidal thoughts, a lack of interest for own state and his family, a lack of projection in the future took place. The patient was diagnosed with major depression. Then, a treatment with amisulpride (150 mg/d) is established. The depressive disorders improved rapidly to disappear after 3 weeks of the treatment.

Case 7

Male subject (38y) diagnosed with bipolar I disorder, most recent episode depressed. His family informed the therapist of a dramatic decrease of his professional performance since 6 months. The patient is admitted for bipolar depression and amisulpride 250 mg/d is initiated. The anxio-depressive element disappears after 3 weeks of treatment. After 2 years treatment with amisulpride 250 mg/d, the patient has still not been subject to any recurrent manic or depressive episode.

Case 8

Female subject (47y) diagnosed with bipolar II disorder, recurrent major depressive episodes with hypomanic episodes). Prescription by her personal doctor of a treatment of clomipramine 100 mg/d seems, according to her family, to have her condition deteriorated with increased anxiety and agitation and provoking sleep disorders. The patient's chart improved after switching to amisulpride 200 mg/d. After 6 months no relapse has occurred.

Case 9

Female subject (51y) diagnosed with bipolar I disorder, most recent episode depressed. After a first therapeutic failure with lithium because of non-compliance she has been treated successfully for 5 years with carbamazepine 800 mg/d. The patient is admitted for bipolar depression with serum level of carbamazepine of 8 mg/L. After 3 weeks of treatment with fluoxetine 20 mg/d only a small improvement is observed. A treatment with amisulpride 150 mg/d is then initiated. After 2 weeks of amisulpride treatment, the patient's depressive condition has almost disappeared. Retrospectively, after 3 years no relapse of depressive or manic episodes have been observed with amisulpride 100 mg/d.

Case 10

Male subject (25y) diagnosed with bipolar I disorder, most recent episode mixed. The manic episode had been treated successfully with an antipsychotic treatment consisting of haloperidol and levomepromazine. The patient however refused to follow a long course treatment because he seemed not, according to himself and his family, present severe symptoms. A treatment of amisulpride 300 mg/d resolved the patient's chart after only one month. After 7 months of treatment with amisulpride any relapse has still not occurred.

Case 11

Female subject (51y) diagnosed with bipolar I disorder, most recent episode depressed. After not responding properly when taking lithium as a monotherapy treatment she has been staying for 4 years on a combination of lithium 1200 mg/d and divalproate 750 mg/d. At admission, her lithium serum level was 0.7 mEq/L and her valproate serum level was 100 mg/ml. The amount of lithium was increased in order to obtain a blood level of 0.9 mEq/L. Despite this modification, her depressive condition continued. A treatment with amisulpride 50 mg/d has then being given to her. After 15 days of treatment, the patient's depressive condition improved. After 4 years with amisulpride, still no manic or depressive relapses have occurred.

Case 12

Female subject (36y) diagnosed with bipolar I disorder, most recent episode depressed. The patient's chart showed the existence of a reactive depressive condition which responded only moderately to viloxazine during adolescence. Prescription of 150 mg of amisulpride led to a recovery of the depressive condition after 4 weeks. No relapse had been observed with the patient after one year of treatment with 50 mg amisulpride.

Case 13

Male subject (19y) diagnosed with bipolar I disorder, most recent episode depressed. The prescription of amisulpride 100 mg/d has shown a progressive improvement and the disappearance of the catatonic condition after 6 weeks of treatment. No relapse had been observed with the patient after two years of treatment with 100 mg/d amisuipride.

Case 14

Male subject (62y) diagnosed with bipolar I disorder, most recent episode depressed. After several manic and depressive episodes the patient seems stabilised with a combination of lithium 1600 mg/d and paroxetine 40 mg/d.

Upon admission at the hospital the lithium serum level are controlled and the treatment with paroxetine is stopped. A treatment with amisulpride 100 mg/d is established. After 3 weeks of treatment, a considerable improvement is obtained allowing the patient to go home. After 3 years of treatment amisulpride 200 mg/d the patient still remains stable.

The invention claimed is:

1. A method of treating bipolar depression in a patient suffering from bipolar I or bipolar II disorders and who has not responded to drugs used to treat said bipolar depression, comprising administering to a patient a therapeutically effective amount of at least one benzamide derivative of the Formula (I)

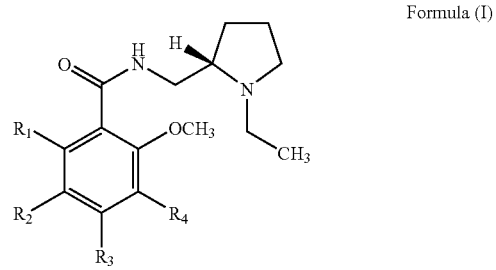

Formula (I)

wherein $R_1$ and $R_4$ are H, $R_2$ is $SO_2C_2H_5$ or $SO_2NH_2$, and $R_3$ is H or $NH_2$, or a pharmaceutically acceptable salt thereof, and wherein said benzamide derivative is the only bipolar disorder therapeutic agent administered.

2. The method according to claim 1, wherein the benzamide derivative of Formula (I) is sulpiride (Ib, with $R_1$=H, $R_2$=$SO_2NH_2$, $R_3$=H, $R_4$=H) or sultopride (Ic, with $R_1$=H, $R_2$=$SO_2C_2H_5$, $R_3$=H, $R_4$=H).

3. The method according to claim 1, wherein the benzamide derivative is administered orally to said patient suffering from bipolar I or bipolar II disorders.

4. The method according to claim 1, wherein the benzamide derivative is administered intravenously to said patient suffering from bipolar I or bipolar II disorders.

5. The method according to claim 1, wherein the benzamide derivative is administered intramuscularly to said patient suffering from bipolar I or bipolar II disorders.

6. The method according to claim 1, wherein the benzamide derivative is amisulpride (Ia, with $R_1$=H, $R_2$=$SO_2C_2H_5$, $R_3$=$NH_2$, $R_4$=H), or a pharmaceutically acceptable salt thereof.

7. The method according to claim 6, wherein the administration is oral.

8. The method according to claim 6, wherein the administration is intravenous.

9. The method according to claim 6, wherein the administration is intramuscular.

10. The method according to claim 6, wherein the amount of amisulpride administered to said patient is from about 20 mg/day to about 800 mg/day.

11. The method according to claim 10, wherein the amount is from about 50 mg/day to about 300 mg/day.

12. The method according to claim 6, wherein the patient is suffering from bipolar I disorder.

13. The method according to claim 6, wherein the patient is suffering from bipolar II disorder.

14. The method according to claim 6, wherein the patient had previously failed to control the bipolar disorder in response to at least one of lithium, divalproate, clomipramine, fluoxetine and paroxetine.

15. The method according to claim 1, wherein the patient had previously failed to control the bipolar disorder in response to at least one of lithium, divalproate, clomipramine, fluoxetine and paroxetine.

* * * * *